(12) United States Patent
Fraziano et al.

(10) Patent No.: US 8,377,910 B2
(45) Date of Patent: Feb. 19, 2013

(54) IMMUNOREGULATOR COMPOUNDS

(75) Inventors: Maurizio Fraziano, Rome (IT); Sanjay Kumar Garg, Chhatishgarh (IN); Antonio Ciaramella, Genazzano (IT); Giovanni Auricchio, Ciampino (IT); Elisabetta Volpe, Rome (IT); Angelo Martino, Monterotondo Scalo (IT); Patrizia Morena Baldihi, Rome (IT); Paolo De Vito, S. Marinella (IT); Domenico Galati, Rome (IT); Vittorio Colizzi, Rome (IT)

(73) Assignee: Universita Degli Studi di Roma "Tor Vergata", Rome (IT)

(*) Notice: Subject to any disclaimer, the term of this patent is extended or adjusted under 35 U.S.C. 154(b) by 1484 days.

(21) Appl. No.: 10/496,497

(22) PCT Filed: Nov. 21, 2002

(86) PCT No.: PCT/IT02/00740
§ 371 (c)(1),
(2), (4) Date: Aug. 17, 2004

(87) PCT Pub. No.: WO03/045365
PCT Pub. Date: Jun. 5, 2003

(65) Prior Publication Data
US 2005/0009757 A1   Jan. 13, 2005

(30) Foreign Application Priority Data
Nov. 21, 2001 (IT) .............................. RM2001A0688

(51) Int. Cl.
*A61K 31/661* (2006.01)
*A61P 31/04* (2006.01)
*A61P 31/06* (2006.01)
*C07F 9/143* (2006.01)

(52) U.S. Cl. ........ 514/114; 514/102; 514/108; 558/158; 558/169

(58) Field of Classification Search ........................ None
See application file for complete search history.

(56) References Cited

U.S. PATENT DOCUMENTS

| | | | |
|---|---|---|---|
| 5,256,641 A | 10/1993 | Yatvin et al. | |
| 5,391,800 A * | 2/1995 | Igarashi et al. | 558/145 |
| 5,430,169 A * | 7/1995 | Boumendjel et al. | 558/169 |
| 5,897,860 A * | 4/1999 | Kim et al. | 424/94.2 |
| 6,147,118 A | 11/2000 | Hugo et al. | |
| 6,239,297 B1 * | 5/2001 | Takesako et al. | 554/58 |
| 6,280,774 B1 * | 8/2001 | Rang | 424/528 |
| 6,667,025 B2 | 12/2003 | Chiba et al. | |
| 2004/0067910 A1 | 4/2004 | Msika et al. | |
| 2006/0134182 A1 * | 6/2006 | Nieuwenhuizen | 424/442 |
| 2006/0252717 A1 * | 11/2006 | Barenholz et al. | 514/44 |
| 2008/0090913 A1 * | 4/2008 | Braxmeier et al. | 514/623 |
| 2010/0278903 A1 * | 11/2010 | Creus | 424/450 |

FOREIGN PATENT DOCUMENTS

| | | | |
|---|---|---|---|
| WO | WO 98/52585 | * | 11/1998 |
| WO | WO 02/48709 | * | 6/2002 |
| WO | WO02/064616 | | 8/2002 |

OTHER PUBLICATIONS

Ruan et al., "Chemical Synthesis of D-Erythro-Sphingosine-1-Phosphate, and Its Inhibitory Effect on Cell Motility", Bioorganic & Medicinal Chemistry Letters, 2(9), 973-978, 1992.*
Dubos, R., Journal of Experimental Medicine, 88, 73-79, 1948.*
Meier et al., Chemical Abstracts, 54:93107, 1960.*
Spiegel et al., Growth Factors and Cytokines in Health and Disease, vol. 1B, 537-563, 1996.*
Garg et al., Journal of Infectious Diseases, 189, 2129-2138, 2004.*
Garg et al., Clinical Immunology, 121, 260-264, 2006.*
Hla, T., Pharmaceutical Research, 47, 401-407, 2003.*
Santucci et al., Biochemical and Biophysical Research Communications, 361(3), 687-693, 2007.*
Johansen et al. "Biochemical and Molecular Analysis of Phospholipase C and Phospholipase D Activity in Mycobacteria", Infection and Immunity, 3259-3266, Aug. 1996.*
Orlati et al., Archives of Biochemistry and Biophysics, 375(1), 69-77, Mar. 1, 2000.*
Kusner et al., The Journal of Immunology, 167(6), 3308-3315, Sep. 15, 2001.*
Akaki, T. et al, "Comparative roles of free fatty acids with reactive nitrogen intermediates and reactive oxygen intermediates in expression of the anti-microbial activity of macrophages against *Mycobacterium tuberculosis*", Clin. Exp. Immunol., 121, 302-310, 2000.*
Remer, K.A.. et al., "Nitric Oxide is Protectie in Listeric Meningoencephalitis of Rats", Infection and Immunity, 4086-4093, Jun. 2001.*
Ohanian, J. et al., "Sphingolipids in Mammalian Cell Signalling", CMLS Cellular and Molecular Life Sciences, 58, 2053-2068, 2001.*

(Continued)

*Primary Examiner* — Fiona T Powers
(74) *Attorney, Agent, or Firm* — Shelly Guest Cermak; Cermak Nakajima LLP

(57) ABSTRACT

The invention relates to sphingosine derivative compounds, like D-erythro-sphingosine 1-phosphate (S1P), to be used as immunomodulators in a microbicidal treatment of infections derived from bacteria and specifically *Mycobacterium tuberculosis*. Such compounds are characterized in that they stimulate macrophagic Phospholipase D (PLD) (FIG. 1). The invention further relates to pharmaceutical compositions containing sphingosine derivative compounds and diagnostic methods for the preparation thereof. Further objects of the invention are methods of inducing or restoring the microbicidal activity in vitro of macrophages for monitoring the efficiency of phagocytosis and degradation processes performed by the same and assay methods suitable to evaluate therapeutic effectiveness of candidate microbicides.

16 Claims, 10 Drawing Sheets

OTHER PUBLICATIONS

Anderson et al., T-cell proliferative response to antigens secreted by *Mycobacterium tuberculosis, Infection and Immunity*, 1991, 59:1558-1563.

Desai et al., Sphingosine 1-phosphate, a metabolite of sphingosine, increases phosphatidic acid levels by phospholipase D activation. *J. Biol. Chem.*, 1992, 267:23122-23128.

Freidag et al., CpG oligodeoxynucleotides and interleukin-12 improve the efficacy of *Mycobacterium bovis* BCG vaccination in mice challenged with *M. tuberculosis, Infect. Immun.*, 2000, 68:2948-2953.

Kusner et al., ATP-induced killing of virulent *Mycobacterium tuberculosis* within human macrophages requires phospholipase D. *J Immunol.*, 2000, 164:379-388.

Kusner et al., Activation of phospholipase D is tightly coupled to the phagocytosis of *Mycobacterium tuberculosis* or opsonized zymosan by human macrophages. *J. Exp. Med.* 1996, 184:585-595.

Liscovitch et al., Phospholipase D: Molecular and cell biology of a novel gene family. *Biochem J.*, 2000, 345:401-415.

Mielke et al., Cytokines in the induction and expression of T-cell-mediated granuloma formation and protection in the murine model of listeroisis, *Immunol Rev.*, 1997, 158:79-93.

Murata et al., Quantitative measurement of sphingosine 1-phosphate by radioreceptor-binding assay, *Analytical Biochem.*, 2000, 282:115-120.

Pfeifer et al., Beryllium-induced disturbances of the murine immune system reflect some phenomena observed in sarcoidosis, *Int. Arch Allergy Immunol.*, 1994, 104:332-339.

Sciorra et al., Potent direct inhibition of mammalian phospholipase D isoenzymes by Calphostin-c. *Biochemistry*, 2001, 40:2640-2646.

Ben-Av, P., et al., "Distinct mechanisms of phospholipase D activation and attenuation utilized by different mitogens in NIH-3T3 fibroblasts," Eur. J. Biochem. 1993;215:455-463.

Gorvel, J. P., et al., "*Brucella* intracellular life: from invasion to intracellular replication," Bet. Microbiol. 2002;90:281-297.

Nathan, C., et al., "Reactive oxygen and nitrogen intermediates in the relationship between mammalian hosts and microbial pathogens," PNAS 2000;97(16):8841-8848.

Pizarro-Cerdá, J., et al., "Subversion of phosphoinositide metabolism by intracellular bacterial pathogens," Nature Cell Biol. 2004;6(11):1026-1033.

Eswarappa, S. M., et al., "Division of the *Salmonella*-Containing Vacuole and Depletion of Acidic Lysosomes in *Salmonella*-Infected Host Cells Are Novel Strategies of *Salmonella enteric* To Avoid Lysosomes," Infection Immun. 2010;78(1):68-79.

Lamothe, J., et al., "*Burkholderia cenocepacia*-induced delay of acidification and phagolysosomal fusion in cystic fibrosis transmembrane conductance regulator (CFTR)-defective macrophages," Microbiol. 2008;154:3825-3834.

Abbott, M., et al., "Haemochromatosis Presenting with a Double Yersinia Infection," J. Infection 1986;13:143-145.

Bhaskaram, P., "Immunobiology of mild micronutrient deficiencies," Brit. J. Nutr. 2001;85:S75-S80.

Lin, M., et al., "Role of iron in NF-kappa B activation and cytokine gene expression by rat hepatic macrophages," Am. J. Physiol.-Gastr. L. 1997;35:G1355-G1364.

Videla, L.A., et al., "Oxidative stress-mediated hepatotoxicity of iron and copper: Role of Kupffer cells," Biometals 2003;16:103-111.

\* cited by examiner

Panel A

Panel B

IMMUNOREGULATOR COMPOUNDS

CROSS-REFERENCE TO RELATED APPLICATION

This application is a National Stage entry of International Application No. PCT/IT02/00740, filed Nov. 21, 2002, the entire specification claims and drawings of which are incorporated herewith by reference.

FIELD OF THE INVENTION

The present invention relates to immunomodulating compounds able to induce, restore or increase the efficiency of immuno-defence mechanisms involved in the early steps of the infection and pharmaceutical compositions containing such compounds.

The present invention further relates to in vitro diagnostic methods for monitoring the efficiency of the phagocytosis and degradation processes performed by macrophages and assay methods of the therapeutic effectiveness of candidate microbicides.

Particularly the invention relates to compounds, compositions and methods relating to the treatment of infections derived from *Mycobacterium tuberculosis*.

STATE OF THE ART

Immuno-defence mechanisms against infective agents include innate and acquired immunity responses developing during the early phases of the infection and later, respectively. Innate immunity is non specific and mediated by the activity of mononuclear, polymorphonuclear phagocytes and Natural Killer cells, whereas acquired immunity is specific and mediated by T and B lymphocytes, which are clonally distributed and characterised by specificity and memory.

Macrophages or mononuclear phagocytes are fundamental cellular components of innate Immune System (SI). These are able to phagocyte and digest exogenous particles by hydrolytic activity of lysosomial enzymes.

Phagocytosis mechanisms are different depending on inert material or microorganisms are involved. In the first case, in fact, phagocytosis is non specific and mediated only by electrostatic forces; in the second, on the contrary, exogenous particle, after coating with complement proteins or antibodies, is phagocytosed by specific recognition mechanism mediated by complement protein or antibody receptors. In any case, the exogenous material, firstly, adheres to the plasmatic membrane of macrophage and then the latter is enveloped within the cytoplasm resulting in a vesicle named phagosome. This reaches the middle of the cell where it is fused with lysosomes, vacuolar organelles rich of hydrolytic enzymes active at acid pH, 4.5-5.0, thus generating phagolysosome. During the maturation process of the phagolysosome therefore there is a progressive acidification of the phagosome whose pH decreases from neutral to acid values, namely 5 or less within the phagolysosome. In the latter almost complete degradation of phagocytosed material occurs, which then is ejected form the cell by means of exocytosis process. The steps of adhesion, ingestion, phagosome formation and phagolysosome maturation involve macrophage activation with the increase of cellular metabolism. Substantially, two anti-microbial systems are exerted by phagocyte: namely, $O_2$-dependent and $O_2$-non dependent system. $O_2$-dependent system uses oxygen reactive intermediates (ROI) as $O_2^-$, $OH°$ and $H_2O_2$, which can act both directly on the pathogens and indirectly through the activation of myeloperoxidase. On the contrary $O_2$-non dependent systems usually act by killing anaerobic bacteria and include a multiplicity of lysosomial enzymes which can be active within the cell or secreted outside, like cationic proteins, lactoferrin and lysozyme. Among $O_2$-non dependent antimicrobial mechanisms in the macrophage there is another important cytotoxic defensive L-arginine dependent system against intracellular pathogens. Such a cytotoxic effect substantially is mediated by nitrogen reactive intermediates (RNI), generated by L-arginine substrate through the activation of inducible form of nitric oxide synthase enzyme (iNOS). The direct association of mycobactericidal effect of murine macrophages with the activation of L-arginine-dependent cytotoxic system was demonstrated. The cytotoxic activity of macrophages therefore results from all the processes hitherto described, whose final goal is to make the macrophage able to eliminate the foreign microorganisms (viruses, bacteria, fungi, protozoa, parasites, etc.).

After phagocytosis by macrophages following intracellular growth of pathogens depends on their capability to avoid the destruction by lysosomial enzymes, reactive oxygen and nitrogen intermediates. Within this context *Mycobacterium tuberculosis*, tuberculosis etiological agent (TB) is able, through various evasion mechanisms, to escape macrophage microbicidal mechanisms.

Tuberculosis currently represents one of three most diffused diseases in the world together with acquired immunodeficiency syndrome (AIDS) and malaria.

An important factor contributing to the increase of MTB occurrence in the industrial countries is represented by the diffusion of drug-resistant strains thereby preventing the elimination of the tuberculosis pathology by means of the usual antibiotic treatments.

A key of MTB virulence is the capability thereof to infect monocytes and macrophages and to replicate therein. Within this context, the mycobacterium can use various macrophage receptors.

After the macrophage phagocytosis, MTB is able to exert a range of mechanisms to escape the macrophage response, such as the production of ammonium ions, resulting in an alkaline intralysosomial compartment. pH increase decreases the enzymatic activity of this compartment which acts, on the contrary, optimally at acid pHs (pH 5), normally maintained by a ATP-dependent protonic pump.

Other mechanisms are represented by the capability of mycobacterium to inhibit the maturation of phagolysosome. Electronic microscopy studies examined dynamics of phagosome-lysosome fusion and effects thereof on the bacterial replication in human infected macrophages and from this study it results that MTB containing vesicles appears to bud from phagosome and separate therefrom without subsequent fusion with the lysosome.

Studies about the interaction of MTB containing phagosomes with the lysosomes in murine macrophages proved inhibition of the phagosome-lysosome fusion, confirmed by subsequent studies also on human macrophages. MTB, in fact, inhibits final maturation events of the phagolysosome biosynthesis. Molecular characterisation of the MTB containing phagosome shows: reduced levels of membrane glycoproteins associated to lysosomes (LAMPs) and cathepsin D, the persistence of Rab5 molecule, characteristic of the early maturation steps and not complete acidification with respect to beads containing phagosomes. Inhibition of phagosome-lysosome fusion represents, in fact, an important evasion strategy of the bactericidal mechanisms because this phenomenon is never found in died bacteria containing phagosomes.

From recent studies about MTB, an important role of a macrophage enzyme in antibacterial response, phospholipase D (PLD), appears. This enzyme is involved in various microbicidal mechanisms of human macrophages and so represents an important component of antibacterial response (Kusner J. D., et al., Activation of phospholipase D is tightly coupled to the phagocytosis of *Mycobacterium tuberculosis* or opsonized zymosan by human macrophages. J. Exp. Med. 1996; 184:585-595).

Phospholipase D (PLD) is a membrane enzyme widely diffused within the mammalian cells whose activity is under the control of hormones, neurotransmitters, growth factors and cytokines. Interaction of extracellular signal molecules with surface receptors activates PLD which catalyses the hydrolysis of phosphatidylcholine (PC) and other phospholipids, generating phosphatidic acid (PA).

PLD activation is associated with various leukocyte antimicrobial mechanisms among which there are phagocytosis, generation of ROI and secreted granules. Particularly the PLD activation in phagocytosis of particles opsonized by the complement or antibodies in neutrophiles and macrophages was demonstrated. MTB phagocytosis by human macrophages is strictly associated with the PLD activation, in fact it was proved that molecules inhibiting PLD activity provoke a reduction of the phagocytic process and administration of exogenous PLD can restore such a process (Kusner et al., "ATP-induced killing of virulent *Mycobacterium tuberculosis* within human macrophages requires phospholipase D", The Journal of Immunology, 2000, 164:379-388).

Although efforts carried out up to now, new and efficient means for treatment of infections able to induce or restore immuno-defence mechanisms, particularly those mediated by phagocyte activity, are still required. Efficient means are more stringently required for infections derived from pathogens like *Mycobacterium tuberculosis* able to develop resistance to currently available medicaments.

However, in view of a practical application in therapeutic field, the promotion of these mechanisms by the administration of exogenous PLD, as suggested by Kusner et al. (supra) results in various problems like immune reactions against protein and allergies. Stability of enzymatic activity when the enzyme is in pharmaceutical formulations represents a further problem. In this context, in the past it was demonstrated that sphingosine 1-phosphate increases phosphatidic acid levels in murine fibroblasts (Desai N. N. et al. "Sphingosine 1-phosphate, a metabolite of sphingosine, increases phosphatidic acid levels by phospholipase D activation" J. Biol. Chem. 1992; 267: 23122-23128). Desai supposes that this PA increase can result from a PLD activation.

The present invention results from the finding that the administration of sphingosine derivatives increases the bactericidal activity of human macrophages.

Increase of microbicidal activity in macrophages is associated to an increase of the macrophage PLD activity and production of reactive oxygen and nitrogen intermediates and induction of the maturation of phagolysosomes in macrophages. Advantageously, administration of sphingosine derivatives, which substance is a constituent of cellular membrane, promotes or restores the endogenous defence mechanisms without the need of using exogenous substances.

SUMMARY OF THE INVENTION

The object of the present invention is to provide new means for the treatment of infections, specifically treatment of the infections derived from pathogens, like *Mycobacterium tuberculosis*, able to develop resistance to currently available drugs, Particularly the object of the present invention is to provide compounds to be used as immunomodulators for a microbicidal treatment able to induce, restore or increase the efficiency of immuno-defence mechanisms involved during the early steps of the infection, principally infections resulting from bacteria and specifically *Mycobacterium tuberculosis*.

Such compounds, which are sphingosine derivatives, like D-erythro-sphingosine 1-phosphate (S1P), are characterised in that they are able to stimulate in a dose-dependent effect the macrophage PLD both in presence and absence of infection.

A further object of the invention is to provide pharmaceutical compositions containing sphingosine derivatives, particularly S1P, and methods for the preparation thereof. These compositions are preferably in the form of solutions, emulsions or suspensions.

Other objects of the invention are methods to induce or restore or increase the in vitro microbicidal activity of macrophages wherein macrophages are infected by a pathogen, preferably MTB and successively treated with sphingosine derivatives.

Other objects of the invention are in vitro diagnostic methods for monitoring the efficiency of phagocytosis and degradation processes performed by macrophages characterised in that macrophages are infected by cells of the specific fluorescein treated pathogen, fluorescence emission is monitored over the time and a fluorescence variation will indicate the occurrence of fusion of phagosomes with lysosomes and maturation of phagolysosomes.

These methods are fluorometric and/or flow cytometric methods based on the sensitivity to acid pHs of fluorescein-derived labelling compounds. pH decrease, which characterises the maturation of phagolysosomes, results in a decrease of the fluorescence emission. Above reported methods are further developed according to the invention in order to provide assay methods able to evaluate the therapeutic efficiency of candidate microbicides characterised in that the capability of promoting, stimulating, increasing or accelerating the maturation of phagolysosomes in infected macrophages is determined in vitro according to the following procedure: macrophages are brought in contact with fluorescein labelled particles susceptible to be phagocytosed and successively treated with candidate antimicrobic; the fluorescence emission is monitored and the maturation of phagolysosomes detected by decrease of fluorescence emission; the decrease of fluorescence emission is compared to the decrease of fluorescence emission detected according to the same procedure in the absence of the candidate microbicide.

In fact immunomodulating substances able to affect the maturation of phagolysosomes in pathogen infected macrophages will be detected due to their ability in modifying the emission profile of the fluorometric signal during the maturation of phagolysosome.

In the panel B the increase of PLD activity (in ordinate) detected in MTB infected, 5 µM S1P treated MTB infected and *M. smegmatis* infected, respectively, at 24 hours after the infection (in abscissa), in comparison to non infected macrophages, is reported. Data of the latter panel is expressed as mean of increments ±D.S. of experiments carried out on cells from three healthy donors. The statistical analysis was carried out comparing the results from MTB infected and S1P treated infected macrophages, respectively.

Figure 4A:
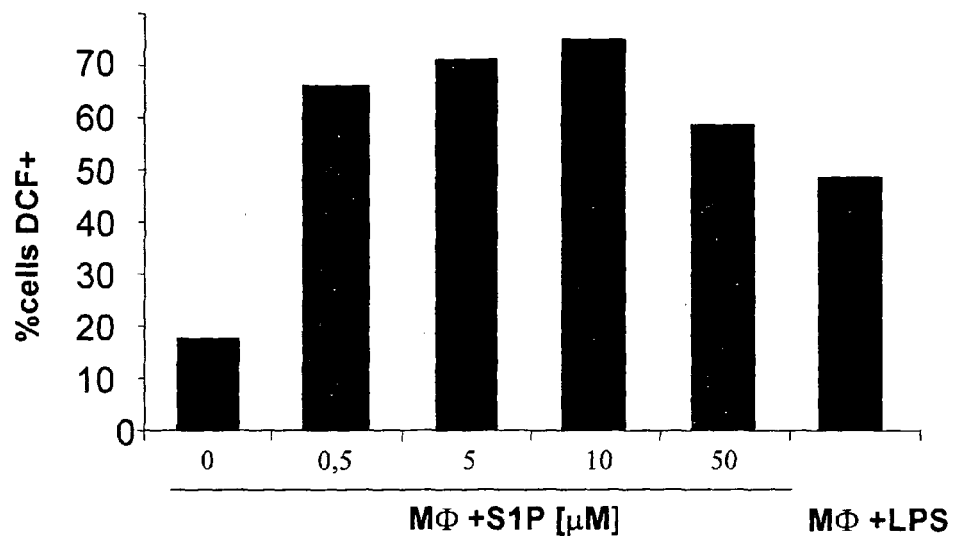
Figure 4B:
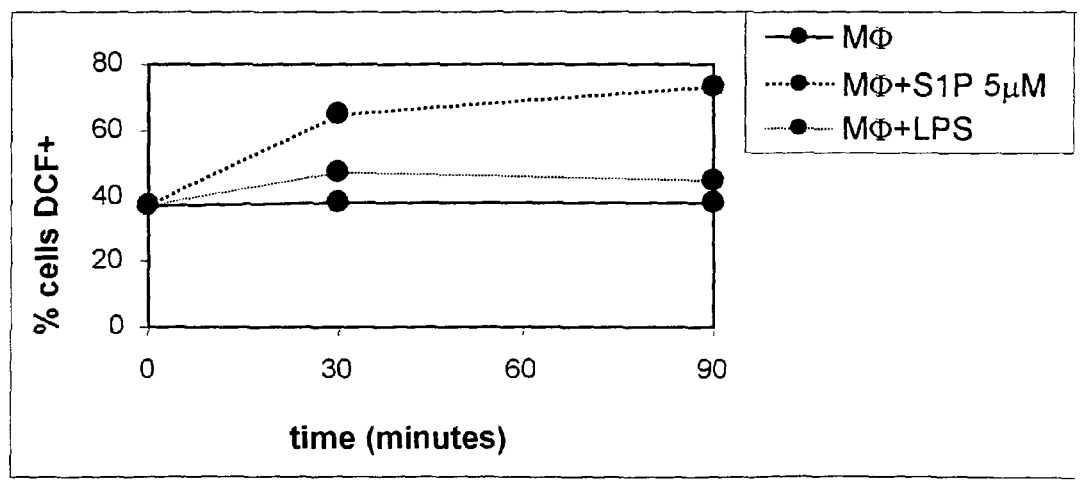

FIG. 4 shows the analysis of ROI generation from S1P treated macrophages. Particularly macrophages (MΦ) were treated by S1P and successively ROI generation was analysed by cytofluorometry, namely using dichlorofluorescein (DCF) assay. In FIG. 4A, in ordinate, % of DCF positive cells obtained at 30 minutes after the treatment with S1P scalar doses, plotted in abscissa, is reported. The graph of FIG. 4B, on the contrary, reports in ordinate % of DCF+ cells at 30 and 90 minutes (abscissa) after the treatment with 5 µM S1P.

Figure 5A:
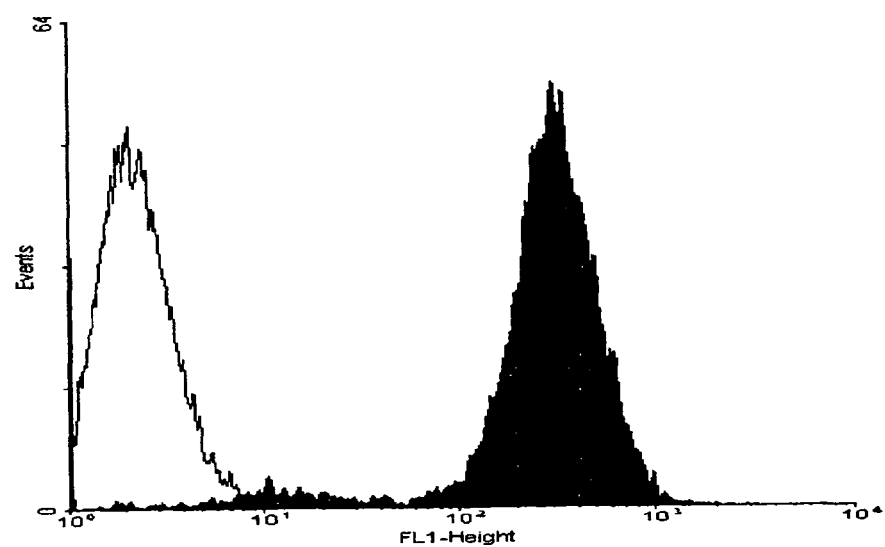

FIG. 5 reports the picture of fluorescein-isothiocyanate conjugated MTB.

Figure 5B:
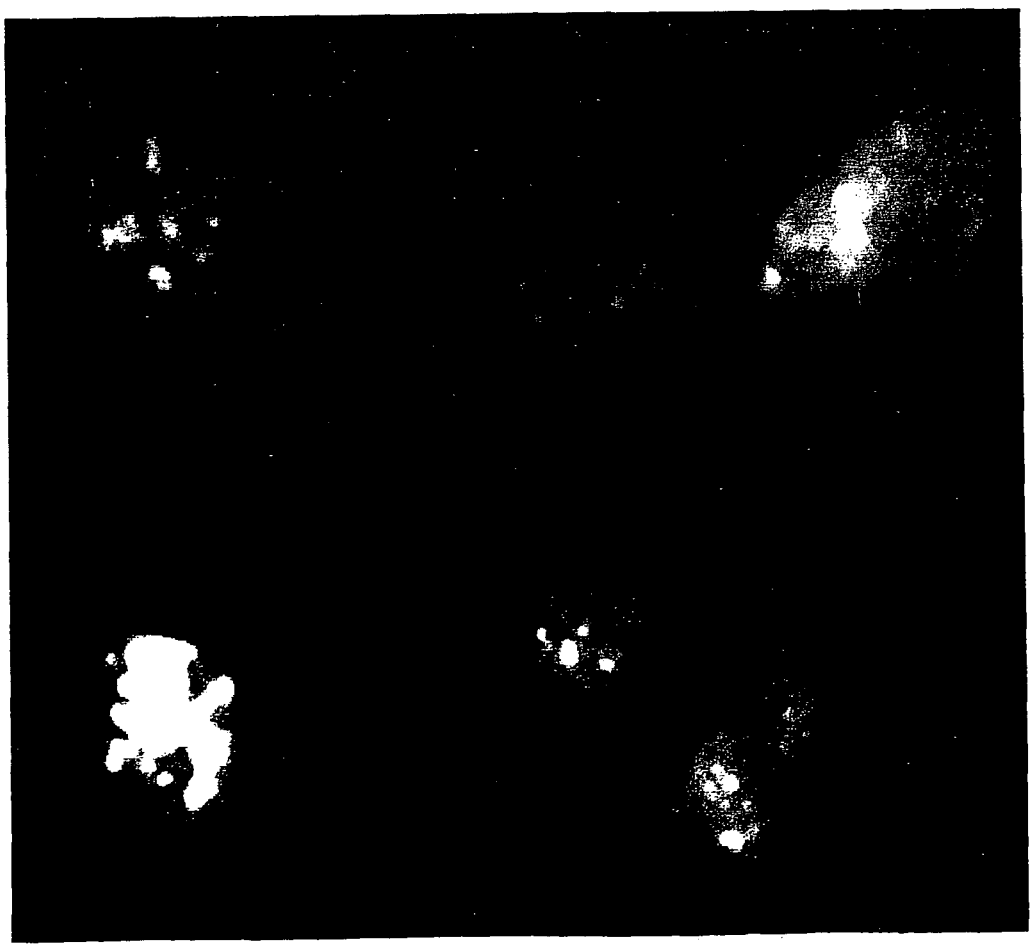

*Mycobacterium tuberculosis* was conjugated to fluorescein-isothiocyanate (FITC) and visualised by flow cytofluorometry (FIG. 5A) and fluorescence microscopy within the macrophages (FIG. 5B).

FIG. 6 shows the analysis of phagolysosome maturation within S1P treated macrophages.

Figure 6A:
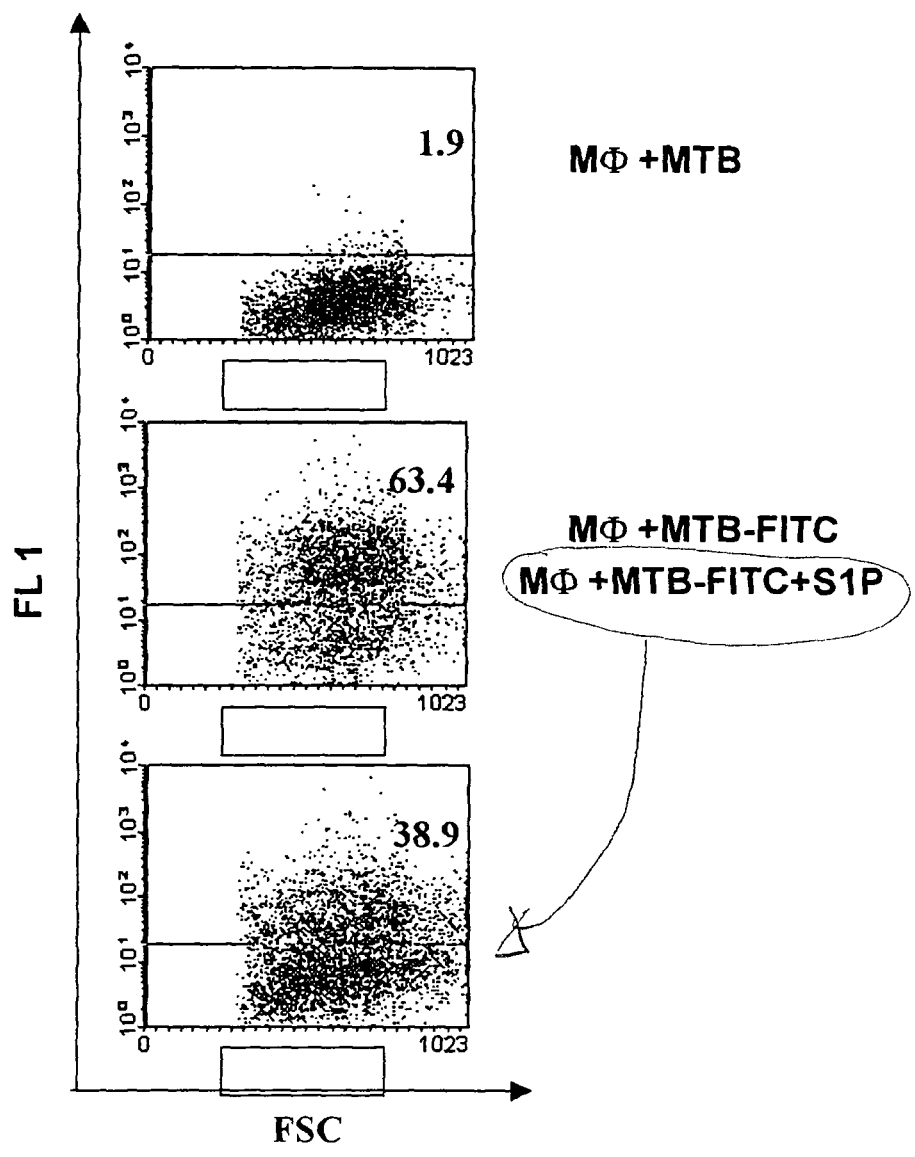
Figure 6B:
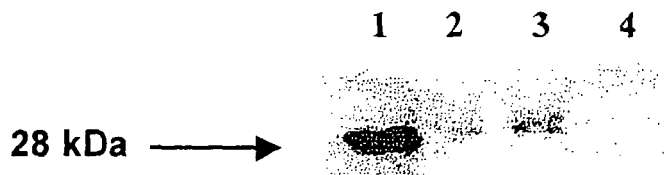

In FIG. 6A there is reported the flow cytometric analysis of MTB-FITC infected macrophages at MOI of a *bacillus* for cell over three hours and 5 µM S1P treated during 30 minutes. For any condition there is reported % of fluorescent macrophages (1.9%, 63.4%, 38.9%). FIG. 6B shows the results of Western blotting of MΦ phagosomial fractions 24 hours after latex beads internalisation. Bands corresponding to 28 kDa refer to intralysosomial Cathepsin D protein of S1P treated (column 3), not treated (column 2), and control macrophages which did not internalise beads (column 4), respectively. Column 1 refers to a positive experiment internal control.

Figure 7:
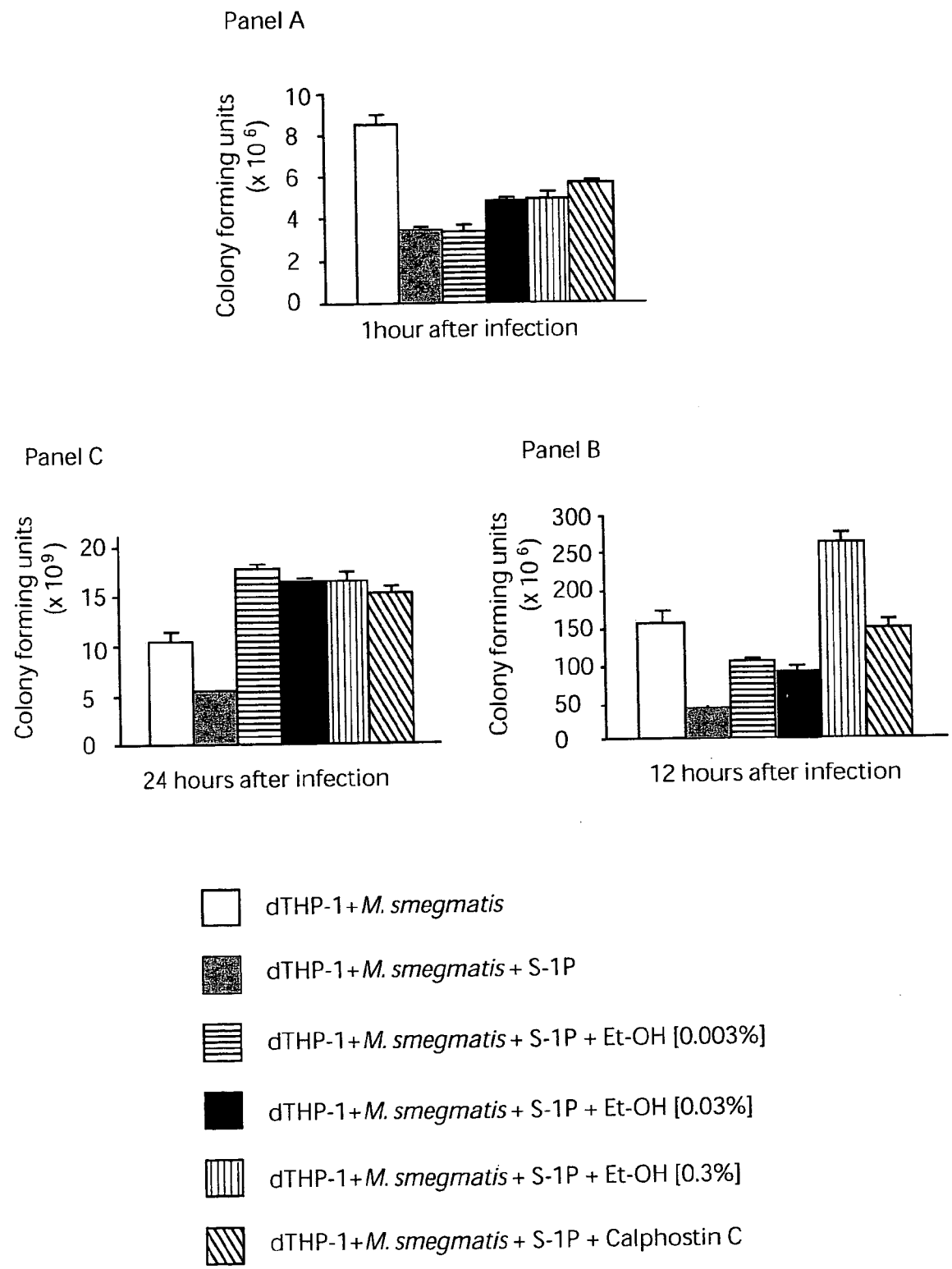

FIG. 7 shows the graphs of the antimicrobial activity of sphingosine 1-phosphate against *Mycobacterium smegmatis*. Mycobacteria are enumerated by an assay of colony forming units carried out at 1 (panel A), 12 (panel B) and 24 hours (panel C) after mycobacterial infection.

Figure 8:
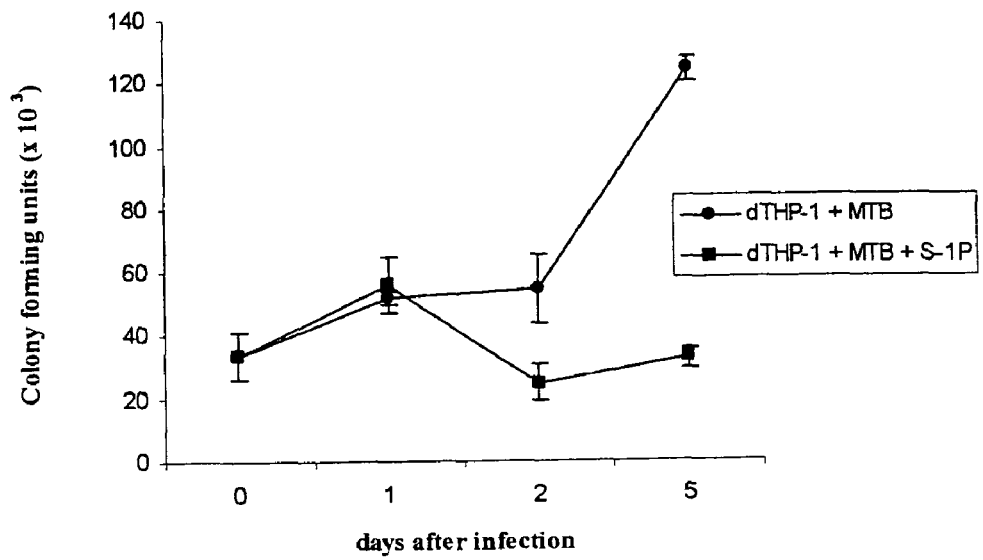
Figure 8:
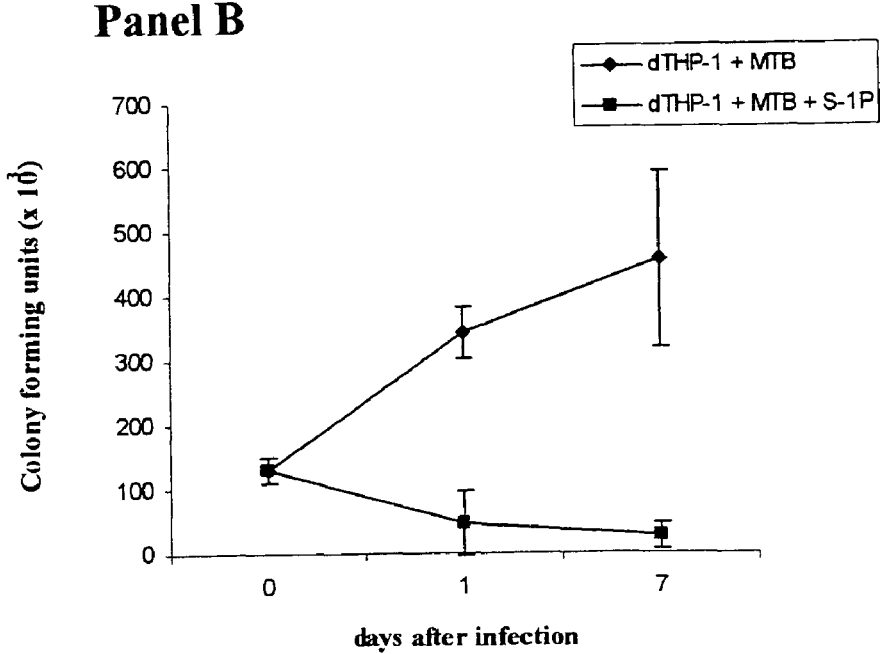

FIG. 8 shows the graphs of the antimicrobial activity of sphingosine 1-phosphate against *Micobacterium tuberculosis*. Infection was carried out with a multiplicity of infection of 1 bacterium for 1 (panel B) and 10 cells (panel A), respectively.

Figure 9:
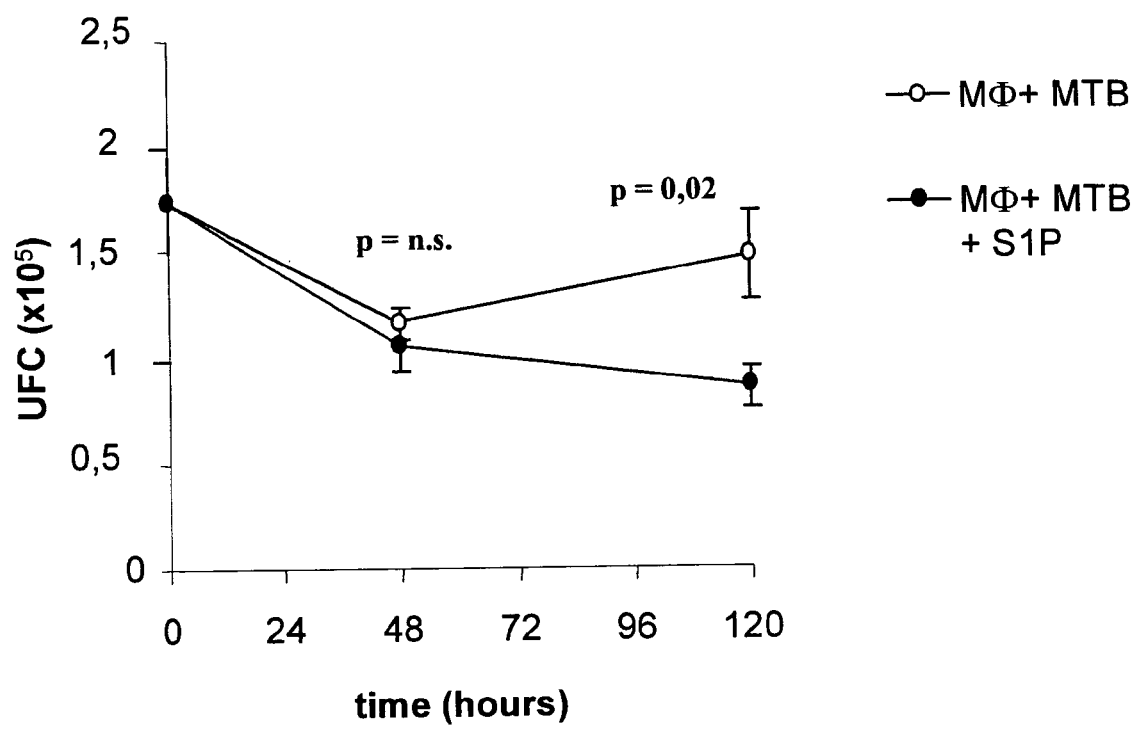

FIG. 9 shows the effect of the S1P treatment on the viability of mycobacteria measured as colony forming units (CFU).

Macrophages (MΦ) were MTB infected at MOI of 1 *bacillus* for 1 cell over 3 hours and treated with S1P (5 µM) for 30 minutes. CFUs, plotted in ordinate, were obtained by plating of intracellular mycobacteria in triplicate immediately (time 0), and at 2 and 5 days after the infection (in abscissa). Obtained results are expressed as mean±DS of triplicate of an experiment representative of two experiments carried out on cells from donors.

Figure 10:
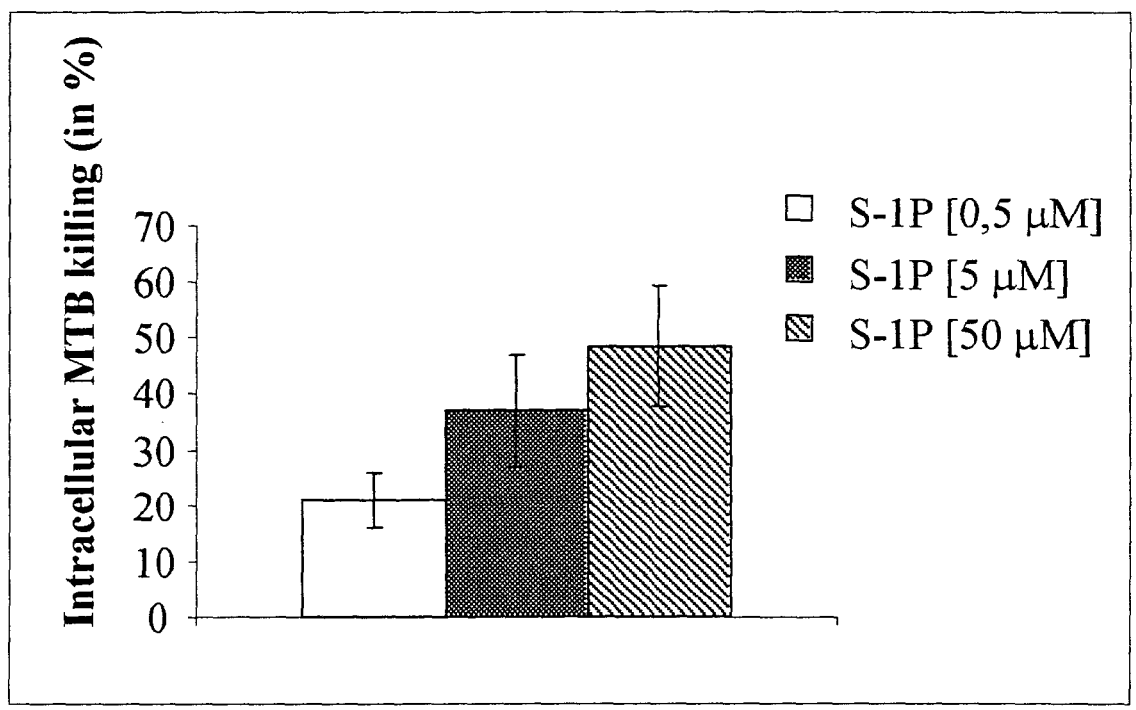

FIG. 10 shows a graph of the intracellular replication inhibition of *Micobactedium tuberculosis* in macrophages derived from peripheral blood from healthy donors using sphingosine 1-phosphate at concentrations of 0.5, 5 and 50 µM, respectively.

DETAILED DESCRIPTION OF THE INVENTION

Immunomodulating compounds according to the present invention are sphingosine derivatives. Sphingosine is a long chain amino alcohol constituent of cellular membranes and together with sphingosine 1-phosphate is a member of a new class of second lipid messengers produced in response to growth factors. Sphingosine itself and its derivatives can be both in erythro and threo conformation, (D) and (L) configuration and cis and trans across the double bond. Sphingosine derivatives are able to mimic immunomodulating activity, particularly those selected among D-erythro or L-threo and monophosphates, diphosphates, triphosphates thereof and more particularly D-erythro sphingosine 1-phosphate (S1P).

Administration of therapeutically effective amounts of sphingosine derivatives induces an increase of microbicidal activity, particularly bactericidal and specifically mycobactericidal of human or animal macrophages which can be detected as a decrease of colony forming pathogen units (CFU). Such an immunomodulating activity is associated to the induction of phagolysosome maturation and increase of the activity of macrophage phospholipase D in pathogen infected macrophages and increase of the production of oxygen and/or nitrogen reactive intermediates.

Therefore the above sphingosine derivative compounds to be used as immunomodulators and for related uses in the preparation of medicaments with immunoregulating activity, e.g. associated to the above phenomena, are object of the present invention.

Sphingosine derivatives as immunoregulating compounds according to the present invention can be used advantageously in the treatment of infections resulting from any pathogen as viruses, bacteria, fungi, protozoa and other parasites and particularly *Mycobacterium tuberculosis* or *Listeria monocytogenes*.

Object of the present invention are also pharmaceutical compositions comprising a therapeutically active amount of a sphingosine derivative compound together with one or more pharmaceutically acceptable adjuvant and/or excipient.

These compositions can contain the immunoregulating compound as the sole active agent when used in a treatment for simple promotion of native immunodefences or can contain the same in association with other microbicidal medicaments.

Pharmaceutical compositions according to the present invention can be formulated according to known methods which include the presence of a pharmaceutically acceptable vehicle both in solid and liquid form. Examples of these vehicles and formulation methods are reported in specialised literature. Pharmaceutical compositions suitable for immunoregulating activity must contain an effective amount of the active principle according to the present invention. In the case of liquid compositions such an amount corresponds to concentrations from 0.1 µM to 1 mM, preferably from 0.5 µM to 10 µM. In the case of solid compositions the amount expressed as µg corresponding to the above concentrations can be used. Pharmaceutical compositions according to the present invention are administered to a subject in a such amount that is effective for successful treatment of the related infection. Relative amount can be varied depending on a multiplicity of factors like individual conditions, weight, sex and age. Preferred formulations are liquid compositions in the form of solutions, suspensions or emulsions to be administered by oral or parenteral route. Due to the chemical characteristics of sphingosine derivatives the inclusion thereof within liposomes or emulsions is particularly preferred. Administration of liquid compositions as spray or aerosol is particularly preferred for the treatment of infected aerial pathways and particularly lung infections as tuberculosis. According to the present invention the immunoregulating compound can be administered typically in mixture with suitable pharmaceutical diluents, excipients or vehicles conveniently selected by taking in consideration the desired administration route.

Because the inventive compounds are soluble in hydroalcoholic solvents (water/ethanol), such solutions thereof are used as such, if suitable, or are used as starting reagent for the preparation of different pharmaceutical formulations. Further, the composition can contain pharmaceutically acceptable optional additives as surfactants, buffers, stabilisers, preservatives and antioxidants.

The preparation of the pharmaceutical compositions according to the invention includes methods known in the specific field. The immunomodulating compounds are mixed in solid or liquid form with suitable excipients, possibly with any desired optional additive, preferably in hydroalcoholic solutions, at concentrations from 0.1 µM to 1 mM, preferably from 0.5 µM to 10 µM or, in the case of solid compositions, at corresponding weight amounts. These solutions are then formulated in liquid compositions suitable to be administered, as solutions, suspensions, emulsions, or liposome encapsulated or dried as powders or granules suitable to be formulated in solid compositions.

Further object of the present invention is an in vitro method to induce or restore or increase the microbicidal activity of phagocytes, preferably human macrophages. Macrophages cultured as described in the experimental section and infected by pathogens susceptible to phagocytosis at a pathogen/macrophage infection ratio (MOI) from 1:1 to 10:1 for a period from 1 to 24 hours are treated with solutions containing sphingosine derivatives according to the invention at concentrations from 0.1 µM to 5 µM, preferably from 0.5 µM to 50 µM, particularly 5 µM over an incubation period from 1 minute to 24 hours, preferably from 15 to 90 minutes. Suitable pathogens are viruses, bacteria, fungi, protozoa, parasites, particularly *Mycobacterium tuberculosis*. In the latter case macrophages are preferably treated with D-erythro sphingosine 1-phosphate.

Figure 3A:
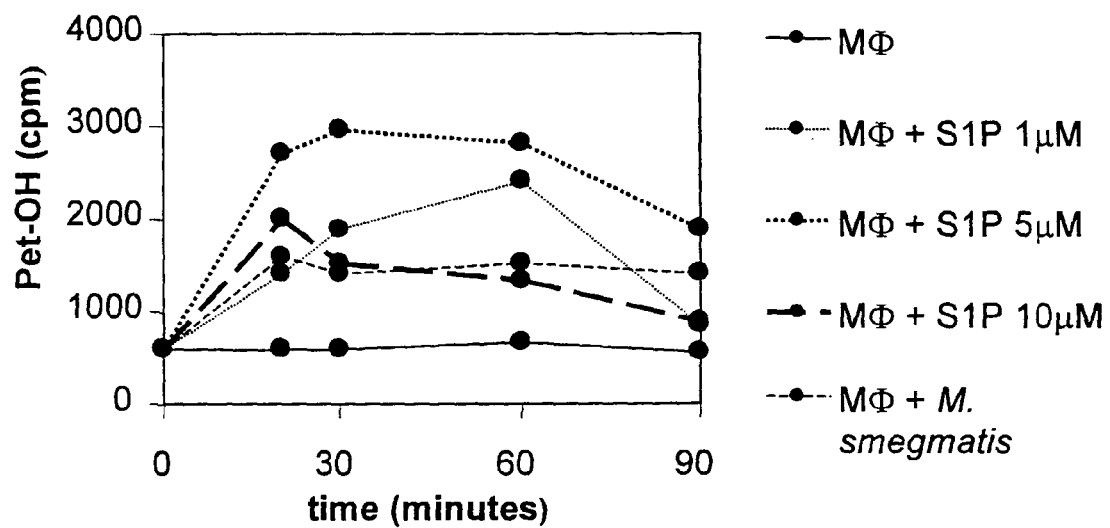
FIG. 3 shows the formation of phosphatidyl ethanol, indicating the activity of macrophage PLD, plotted in ordinate, at 20, 30, 60, 90 minutes after the treatment (in abscissa) with scalar doses (1, 5, 10 µM) of D-erythro-sphingosine 1-phosphate (S1P) (panel A).
Figure 3B:
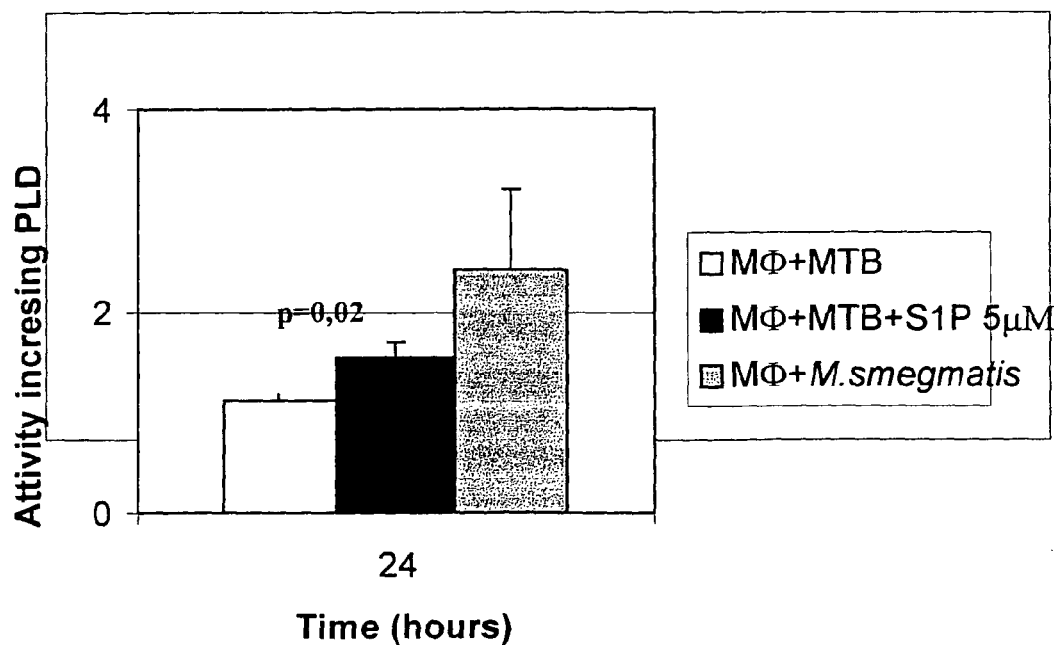

Induction or restoration or increase of the microbicidal activity of macrophages can be monitored in terms of the activity of the macrophage PLD as described in FIG. 3 and example 1. Alternatively the activity of macrophages can be evaluated in terms of generation of oxygen reactive intermediates (ROI), as described in FIG. 4 and example 3 or viability of phagocytised microorganisms as described in FIG. 7 and example 6.

Further object of the present invention is a diagnostic method in vitro to evaluate the efficiency of the processes of phagocytosis and degradation for a specific pathogen carried out by macrophages based on fluorescence techniques. As already discussed the biogenesis of phagolysosomes derived from an exact fusion of phagosomes and lysosomes in pathogen infected macrophages is the essential condition for the occurrence of the degradation action on the phagocytised microorganisms. Therefore the right maturation of the phagolysosomes is an important indication of the antimicrobic efficiency of macrophages. The present diagnostic methods are based on the decrease of pH values within the microsomial fraction during the biogenesis of phagolysosomes and sensitivity to acid pH of fluorescein derivatives like fluorescein isothiocyanate (FITC). Decrease of the pH value results in a decrease of the fluorescence emission from phagosomial fraction or decreased proportion of fluorescence emitting cells.

Microorganisms are labelled with such fluorescent markers, as described in example 4. Then, macrophages are infected by fluorescent microorganisms at a pathogen/macrophage multiplicity of infection (MOI) from 0.1:1 to 100:1, preferably from 1:1 to 10:1 for a period from 1 to 24 hours and the emission of fluorescent signal monitored by means of a fluorometer, flow cytometer or fluorescence microscope as described in FIGS. 5 and 6. According to an alternative embodiment of the method microorganisms can be substituted by synthetic particles, like latex beads, susceptible to be phagocytised by macrophages as reported in example 5.

A further development of the above described methods allows methods suitable to evaluate in vitro the therapeutic efficiency of candidate substances as microbicides according to the present invention to be provided. Carrying out of such methods includes macrophages to come in contact with known microorganisms or synthetic particles, both susceptible to be phagocytised, labelled using above described fluorescein derivatives. After an incubation period, macrophages are treated with the substance whose microbicidal efficiency is to be evaluated for a period of time from 15 to 90 minutes, preferably 30 minutes. Then, fluorescence emission is monitored by means of a fluorometer, flow cytometer or fluorescence microscope detecting the biogenesis of mature phagolysosomes through the emission decrease of fluorescence signal.

Decrease of the fluorescence emission is compared with that observed according to the same procedure in absence of candidate microbicide. Any substance able to promote, stimulate, increase or accelerate the maturation of phagolysosomes in macrophages will be detected being able to modify the emission profile of fluorometric signal when compared to the observed model in the absence of such substance.

The invention is further illustrated by the following examples which describe reagents, conditions and procedure suitable for the practice of the invention but it is understood that the scope thereof is not limited thereto.

EXAMPLE 1

Comparative Analysis of the Macrophage PLD Activity after *M. smegmatis* or H37Rv *M. tuberculosis* Infection 1.1. Microorganisms H37Rv (MTB) *M. tuberculosis* virulent strain was cultured in Sauton medium at 37° C. in unmodified atmosphere, taking care the growth thereof was as surface film. After culturing for about three weeks mycobacteria were washed with PBS (phosphate buffered saline), centrifuged at 14000 rpm for 5 minutes and sonicated for 1-2 minutes. Successively mycobacteria were suspended within the same buffer and then aliquoted and frozen at −80° C.

Culture of *M. smegmatis* non pathogen strain was carried out in ADC enriched Middlebrook 7H9 (DIFCO) liquid medium for three days in incubator at 37° C. and 5% $CO_2$ containing atmosphere. Finally the bacteria were aliquoted and frozen at −80° C.

Before the freezing, serial dilutions of initial bacterial suspension were carried out. Such suspensions then were seeded in plates containing OADC enriched 7H10 agar. The number of colony forming units was evaluated at about 4 weeks and 3 days of MTB and *M. smegmatis* culturing, respectively. Bacteria concentrations of initial aliquots, both of which were about $10^9$ bacteria/ml, were deduced from the number of such colonies.

In some experiments MTB aliquots, after thawing at room temperature, centrifuged at 10000 rpm for 10 minutes, suspended in PBS and sonicated for 1-2 minutes, were labelled with fluorescein isothiocyanate (FITC) (Sigma). FITC, presuspended at 1 µg/ml concentration, was added to the bacterial suspension, which was incubated at 37° C. in the presence of 5% $CO_2$ for about 90 minutes. At the end of the incubation the bacterial suspension was washed three times with centrifugation at 14000 rpm for 15 minutes and suspended in PBS at required concentration.

1.2. Purification of Mononuclear Cells from Peripheral Blood and Separation of Monocytes.

Mononuclear cells from peripheral blood were isolated from healthy donor buffy-coat by stratification on Lymphoprep (Eurobio, density ~1.077) lymphocyte separation medium and centrifugation at 1800 rpm for 20 minutes. Interface recovered cells were washed three times in RPMI 1640 (GIBCO). First, second and third centrifugation were carried out at 1600, 1400 and 1000 rpm for 15 minutes, 10 minutes and 10 minutes, respectively. Cells were suspended in RPMI complete medium, i.e. with addition of 10% FBS, gentamicin (used at 50 µg/ml) and L-glutamine (used in at 1%). Monocytes were separated from lymphocytes by adherence in flask. To that end, 15 ml of cellular suspension were stratified in 75 $cm^2$ polystirene flasks (Corning) and incubated for 1 hour at 37° C. in 5% $CO_2$ containing atmosphere. Non adherent cells were removed by three wahings with warm RPMI pre-heated at 37° C. Adherent cells corresponding to monocyte/macrophage population were removed from the bottom of the flask after incubation at 4° C. with cold PBS for about 30 minutes. As detected by flow cytometric analysis of cell physical parameters, i.e. FCS dimension and SSC granulometry, minimal purity thereof was always higher than 80%.

Cells were cultured in 24 well plates (Costar) at $1×10^6$ cell/ml concentration for 7 days in order to obtain macrophages (MΦ) and incubated in the presence or absence of IFNγ (500 U/ml) depending on the experiment.

1.3. Macrophage Infection with *M. tuberculosis* or *M. smeamatis* and Treatment with D-erythro sphingosine 1-phosphate.

Before the macrophage (MΦ) infection the bacteria were thawed at room temperature. Then, three PBS washes were carried out at 10000 rpm for 10 minutes. Being prone to aggregate mycobacteria were transferred in glass tubes and bath sonicated to allow cellular separation. Infection of monocyte derived macrophages was carried out in culturing plates with incubation of the cells for three hours with H37Rv MTB or *M. smegmatis* at infection ratio of bacterium/cell 1:1. At the end of the infection the plates were centrifuged at 1800 rpm for 10 minutes and supernatant discarded. Then, the cells were suspended in complete medium, treated with D-erythro-sphingosine 1-phosphate (Calbiochem) at concentrations reported time by time in the individual experiment and finally separated from the bottom of the well and analysed.

1.4 Assay of PLD Activity

A system for the detection of phosphatidyl ethanol (Pet-OH), a stable product from the PLD catalysed transphosphatidylation reaction in the presence of ethanol within the medium, is used for the determination of macrophage (MΦ) PLD activity. Macrophages, suspended at $1×10^6$ cell/ml concentration in 24 well plates, were incubated with [$^3$H]-miristic acid at 1 µCi/ml/well concentration for 180 minutes at 37° C. in RPMI complete medium in order to label fatty acids of plasmatic membrane. After three washes with warm RPMI, cells were incubated with 1% ethanol for 15 minutes and then infected with *M. smegmatis* or MTB at 1:1 bacterium/cell multiplicity of infection. After 3 hour infection cells were centrifuged at 1800 rpm for 10 minutes, suspended in Hepes 20 mM (pH 7.3), centrifuged and again suspended in Hepes 20 mM (pH 7.3) and methanol at 1:1 ratio. Finally the cells were separated and collected in test tubes to which 2 ml of a solution containing chloroform/methanol 1:1 were added. After agitation of the suspension chloroform (1 ml) and KCl (1 ml) were added and again agitated. Two phases could be seen: a lower chloroform containing phospholipids, neutral lipids and other liposoluble compounds and an upper water phase containing polar substances. Successively the lower chloroform phase was recovered and transferred in fresh tubes, dried under nitrogen and suspended in 20 µl of chloroform.

Separation of Pet-OH from other phospholipids was carried out by monodimensional thin layer chromatography on plates activated at 100° C. for 1 hour, just before the use. Ethyl acetate/iso-octane/acetic acid/bidistilled water (130/20/30/100 v/v) was used as solvent system. The spots detected with vapor phase iodine were removed from the plate and the gel was transferred in test tubes in the presence of 200 µl of ethanol to enhance lipid solubilisation and 3 ml of scintillation liquid. Test tubes were then transferred in a liquid scintillation counter for the measurement of beta rays emitted from incorporated labelled fatty acids.

1.5 Results

Figure 1:
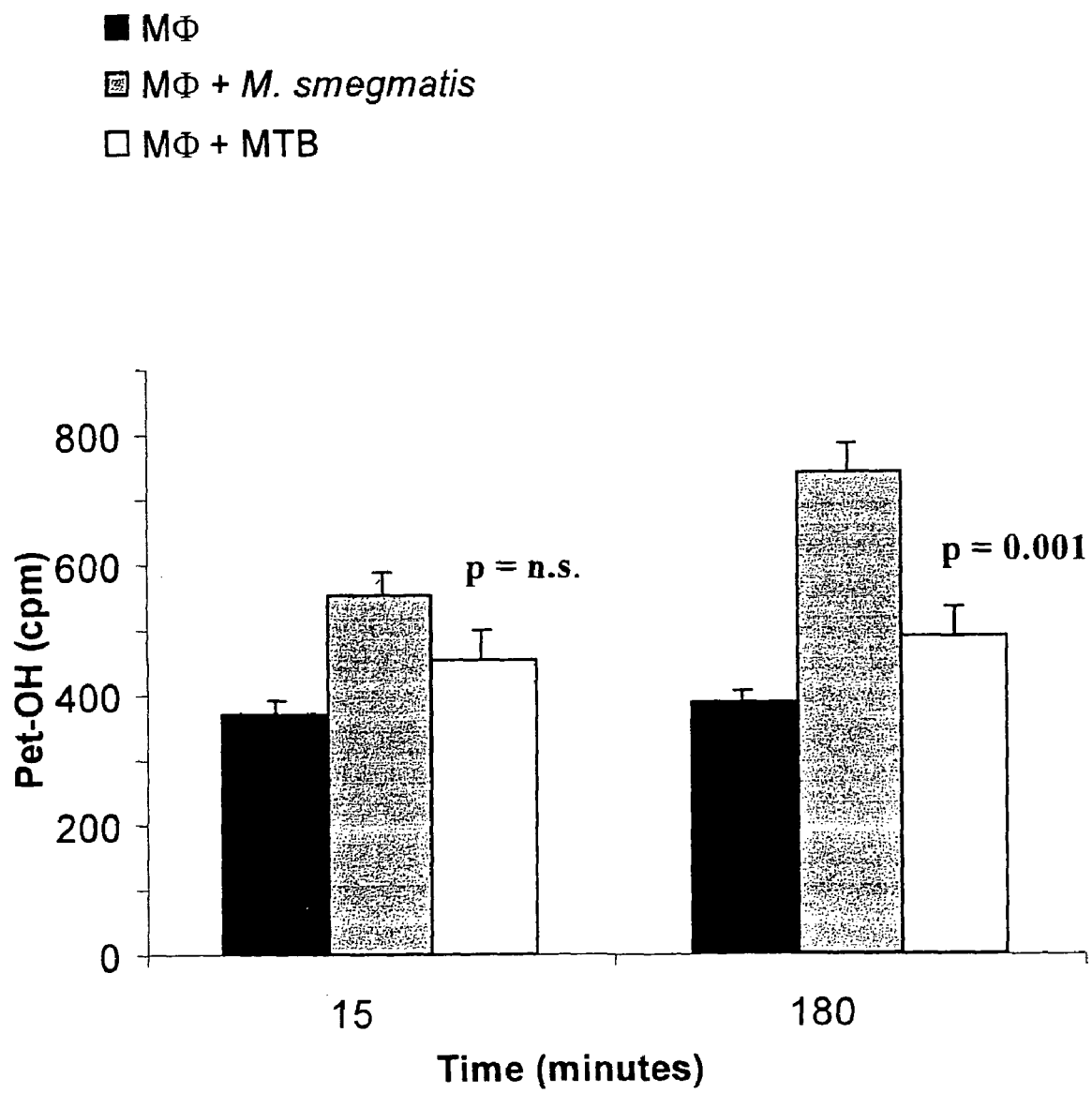
FIG. 1 shows comparative analysis of PLD activity of IFN-γ-stimulated macrophages after *M. smegmatis* or MTB infection. Macrophages (MΦ) were infected by *M. smegmatis* or MTB at MOI of a *bacillus* for cell. The formation of phosphatidyl ethanol, indicating the activity of macrophage PLD, plotted in ordinate, was measured at 15 and 180 minutes after the infection, and plotted in abscissa. The results are expressed as mean±DS of triplicate of an experiment representative of experiments carried out on cells from three different donors. The statistical analysis was carried out comparing the results from *M. smegmatis* and MTB infected cells, respectively.

Based on recent studies demonstrating the antimycobacterial effect of phospholipase D (PLD) it was decided to analyse the human macrophage PLD activity after mycobacterium infection. In order to point out a correlation between PLD activation and mycobacterium pathogenicity, PLD activities in macrophages (MΦ) from healthy donors infected with non pathogenic, i.e. *Mycobacterium smegmatis*, or pathogenic, i.e. *Mycobacterium tuberculosis* (MTB), were compared. Behaviour of macrophage PLD in the early phases of the mycobacterium infection was monitored by infecting cells with *M. smegmatis* or *M. tuberculosis* and assaying the PLD activity at 15 and 180 minute following the exposure to mycobacterium. Infection in our experiments was carried out at the infection multiplicity (MOI) of 1 *bacillus* for cell and analysis of the PLD activity was performed using as index the formation of phosphatidyl ethanol (Pet-OH) generated by PLD catalysed transphosphatidylation reaction, 1% ethanol being present within the culture medium. Obtained results are represented in FIG. 1 and it is possible to see that cells exposed both to the pathogenic and non pathogenic mycobacterial strains show PLD activity levels higher than non infected macrophages and the exposure to a non pathogenic bacterium results in macrophage PLD activation significantly higher than MTB, 180 minutes following the infection. This indicates that simple exposure to mycobacteria stimulates a strong and early PLD activation which is inversely proportional to the mycobacterium pathogenicity.

EXAMPLE 2

Figure 2A:
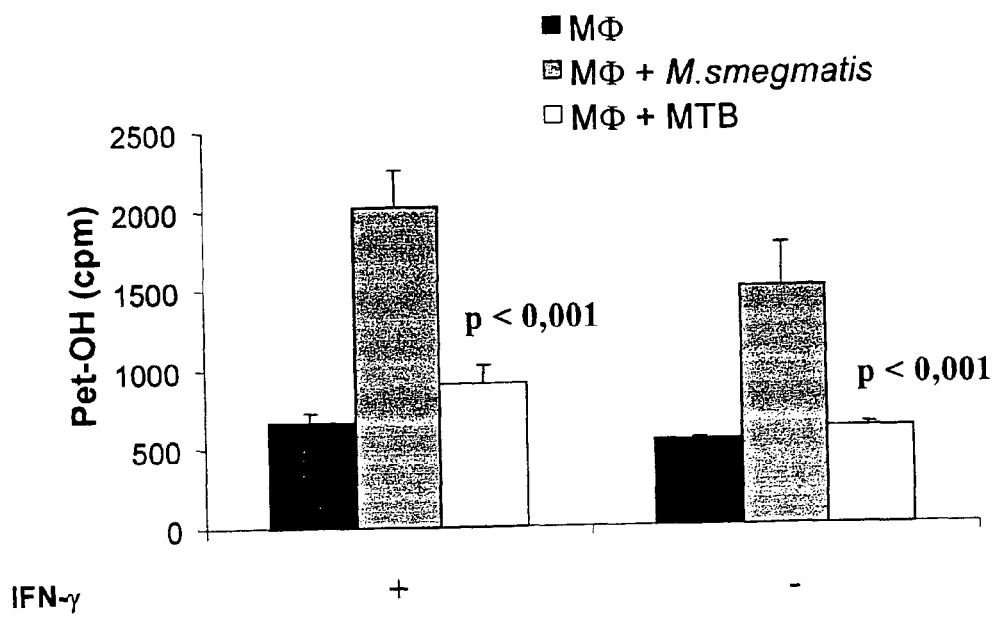
FIG. 2 shows the formation of phosphatidyl ethanol, indicating the activity of macrophage PLD, plotted in ordinate, of IFN-γ-stimulated macrophages after *M. smegmatis* or MTB infection. Macrophages were infected by *M. smegmatis* or MTB at MOI of a *bacillus* for cell. PLD activity was measured at 3 (A panel) and 24 (panel B) hours after the infection, in the presence (+) or absence (−) of IFN-γ. Results are expressed as mean±DS of duplicate of experiments carried out on cells from two different donors. The statistical analysis was carried out comparing the results from *M. smegmatis* and MTB infected cells, respectively.
Figure 2B:
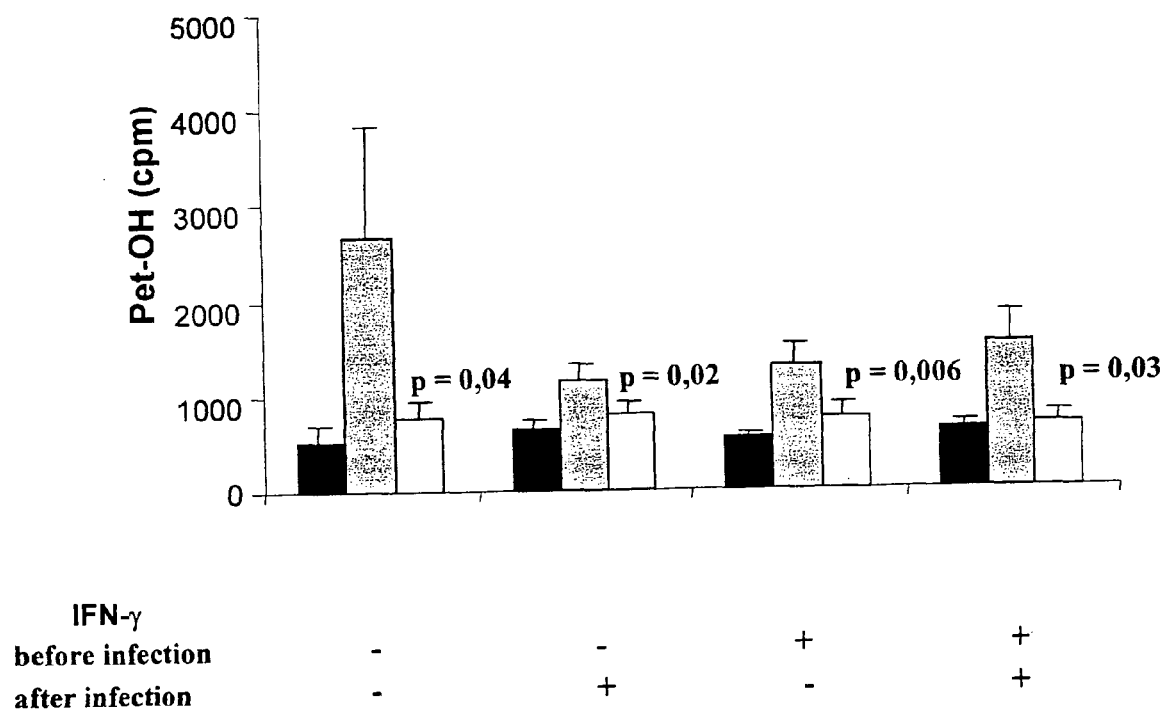

Analysis of PLD Activity of IFN-γ-Stimulated and
M. smeqmatis or M. tuberculosis H37Rv Infected
Macrophages In order to point out possible correlation between macrophage activation state and PLD stimulation following mycobacterial infection, cells were treated with IFN-γ (500 U/ml), before and after the infection. FIG. 2 shows the formation of phosphatidylethanol, indication of macrophage PLD activity, generated in macrophages 3 hours (panel A) after MTB or M. smegmatis infection. Such an experiment confirms previously obtained results and points out that IFN-γ pre-treatment of the infected macrophages does not modify the behaviour of the PLD activity, excluding any effect of IFN-γ mediated cellular activation on PLD activity.

In order to analyse the behaviour over the time of the macrophage PLD activity following mycobacterial infection the experiment was repeated and cells analysed 24 hours after the infection. Results are reported in panel B and as can be seen M. smegmatis infection causes a PLD increment higher than MTB. Further it is possible to point out that IFN-γ treatment before and/or after infection does not appear to modify levels of macrophage PLD activity following mycobacterial infection.

EXAMPLE 3

Analysis of Macrophage PLD Activity Following
D-erytho-sphingosine 1-phosphate Treatment From above experiments it was found out that PLD activity levels of MTB infected macrophages are lower than M. smegmatis infected macrophages. Object of this experiment was to increase levels of the endogenous PLD activity of MTB infected macrophages by means of D-erythro sphingosine 1-phosphate (S1P). In order to test the efficiency of this molecule and find out optimum dose for the macrophage maximum activation the latter were treated by scalar S1P doses and cell PLD activity was analysed after 20, 30, 60, and 90 minutes. As can be seen from FIG. 3A in the S1P treated macrophages, maximum activation is obtained after 30 minutes and using a S1P 5 μM concentration. Following the assay of the S1P efficiency on the macrophage PLD, the effect thereof on MTB infected cells was evaluated in order to increase the PLD activation levels of pathogenic mycobacterium infected macrophages. Cells were MTB infected under the same conditions as in above experiments and macrophage PLD activity was analysed 24 hours after infection. Results are reported in FIG. 3B and as can be seen MTB infected and S1P treated macrophages show a Pet-OH production, index of PLD activity, higher than MTB infected non S1P treated ones, indicating that S1P causes increase of PLD activity of MTB infected macrophages.

EXAMPLE 4

Analysis of Oxygen Reactive Intermediates
Generated from D-erythro-sphingosine 1-phosphate
Treated Macrophages 4.1 Flow Cytometry—Analysis of ROI Generation from dichloro fluorescein Because dichloro fluorescein (DCF) is a fluorochrome obtained from reaction of non fluorescent 2,7-dichloro fluorescein diacetate (DCFH) with various oxidants, analysis thereof is used to detect cellular oxidative stress and amount of oxygen reactive intermediates (ROI) produced by phagocytic cells. In the used model, this analysis is employed in order to monitor the D-erythro-sphingosine 1-phosphate (S1P) modulated ROI production from macrophages. Macrophages were incubated for 90 minutes with sphingosine 1-phosphate at 0.5 μM, 5 μM, 10 μM and 50 μM concentrations. After the incubation 100 μl of 0.4 μM DCFH (Calbiochem) were added and incubated for at least 30 minutes. Finally, cells were washed with PBS and analysed using FACScan flow cytometer from Becton Dickinson.

4.2 Results

It is already known that PLD is involved in anti-microbial activities like generation of oxygen reactive intermediates (ROI) and, in order to test this property, ROI amount was monitored after macrophage PLD modulation by S1P. Measure was carried out using dichlorofluorescein (DCF), fluorescence emitting molecule when bound to these oxidative products of phagocytic cells so that it is detectable by flow cytometry. From panel A of FIG. 4 it is observed that non treated cells show low levels of DCF positive response indicating the minimal amount of oxygen reactive intermediates produced by macrophages in standard conditions. When cells are stimulated by lipopolysaccharides, which induce a known increase of ROI generation, an increase of DCF positive cells is observed, resulting in the reliability of the system efficiency for the evaluation of cell produced ROI amount. When cells are treated with S1P scalar doses they show increasing and proportional levels of DCF positive response with maximum at 5-10 μM. In order to analyse over the time the modulation of oxygen reactive intermediate production by S1P the experiment was repeated using 5 μM S1P treated macrophages and measuring DCF positive response after 30 and 90 minutes. Results are reported in panel B of FIG. 4 and as can be seen the ROI production by macrophages increases progressively over the time after the S1P PLD stimulation in comparison to non LPS stimulated or to activated macrophages.

EXAMPLE 5

Fluorescence Analysis of FITC-Conjugated MTB
Infected Macrophages 5.1 Flow Cytometry—Analysis of Phagolysosome Maturation by Means of Infection with Fluorescein Treated MTB By virtue of extreme sensitivity of fluorescein isothiocyanate (FITC) to acid pHs this molecule was used to monitor the phagosome acidity and have therefore information about maturation stage of phagolysosome. To this aim, bacteria were labelled with fluorescein isothiocyanate (FITC) as above described. Infection was carried out using FITC labelled bacteria. Then, cells were washed after 3 hours and stimulated for 30 minutes with 5 μM sphingosine 1-phosphate and following 1.5% paraformaldehyde (PFA) fixated and finally monitored by flow cytofluorometry.

5.2 Fluorescence Microscopy

Fluorescence microscopy was used to detect fluorescein treated M. tuberculosis infected macrophages. Cellular suspension containing $10^5$ macrophages was spread over microscopy slide, allowed to adhere over 16-18 hours in humid atmosphere within a Petri dish and infected with fluorescein treated H37Rv M. tuberculosis strain at 10:1 bacterium-phagocyte ratio. Successively, cells were washed with PBS and fixed with a solution of PBS and 2% para formaldehyde for 30 minutes. Cells were then washed twice and incubated for 5 minutes with PBS and 0.05% saponin. Finally after three PBS washes the slide was observed with fluorescence microscope and then photographed.

5.3 Results

In order to obtain a flow cytometric system suitable to monitor mycobacterial infection in macrophages a bacterium staining method with fluorescein isothiocyanate (FITC) was provided. Conjugation of H37Rv MTB with fluorochrome was monitored by flow cytometry and the same can be observed in panel A of FIG. 5. Then, macrophages were infected with MTB virulent strain, which had been labelled previously with fluorochrome, directly over the slide. Analysis, carried out with fluorescence microscope and shown in panel B, reveals the intracellular localisation of the bacteria, proving that it is possible to infect macrophages with thus previously treated mycobacteria.

EXAMPLE 6

Analysis of the Phagolysosome Maturation within D-erythro sphingosine 1-phosphate Treated Macrophages 6.1 MTB-FITC In order to evaluate the effect of S1P on a specific antimicrobial activity as the maturation of phagolysosome, the infection with FITC-labelled MTB was carried out and the fluorescence values of FITC-MTB were used as indicators of the phagolysosome maturation. In fact such a process is associated with a progressive reduction of phagolysosomial pH and FITC, used to label the mycobacterium within the macrophage phagosome, is sensitive to acid pH. Based on the known capability of M. tuberculosis in reducing the phagosome-lysosome fusion in order to inhibit lysosomial degradation, an attempt to promote and increase the process through exogenous stimulation of PLD by means of S1P was carried out. In FIG. 6 (panel A) it can be seen that the FITC-MTB fluorescence from S1P treated macrophages is reduced from 63.4% to 38.9% when compared to S1P non-treated macrophages.

6.2. Internalisation of Latex Beads

In order to analyse the expression of an intralysosomial protein within beads containing phagolysosomes the macrophage phagosomial fraction was separated. Particularly, cells were incubated with sterile latex beads (0.8 µM diameter) (Sigma), 1:200 diluted, in culture medium for 1 hour in the presence of 5% $CO_2$ and then treated with 5 µM S1P.

6.2.1. Separation of the Macrophage Phagosomial Fraction.

Separation of the phagosomes was carried out by centrifugation on sucrose gradient. Cells were washed three times with PBS (twice for 10 minutes) and then again incubated for 24 hours at 37° C. Following the internalisation and 24 hour incubation period cells were washed with cold PBS and collected using a little scraper in PBS at 4° C., then centrifuged at 2000 rpm for 10 minutes at 4° C. and finally washed with homogenising buffer (250 mM sucrose, 3 mM imidazole, pH 7.4) again at 4° C. Cellular pellet was suspended in 1 ml homogenising buffer and cells were lysed with an homogenizer. Phagosomes were isolated by centrifugation on sucrose gradient. Cells, suspended in 1 ml of PBS, were added to 1 ml of 40% sucrose solution and such a suspension was stratified on 2 ml of 62% sucrose solution in ultracentrifuge tubes. Then 2 ml of 35%, 25% and 10% sucrose solutions were stratified (all the solutions were prepared in 3 mM imidazole, pH 7.4). The tubes were ultra-centrifuged using SW41 rotor at 100000 g at 4° C. The phagosomes were collected at the interface between 10% and 25% sucrose solutions and suspended in 12 ml of cold PBS. Phagosomes were centrifuged at 40000 g at 4° C. and suspended in 100 µl PBS.

6.2.2. SDS-PAGE and Western Blot.

Analysis of intralysosomial protein, cathepsin D, in the phagosomal fractions was carried out by Western blot. Proteins from phagosomal fractions were separated by SDS-PAGE. Polyacrylamide gel in a non continuos buffering system comprising two overlying gels, i.e. "running" and "stacking" gel, respectively, was prepared. The latter is characterised by a lower acrylamide content, ionic strength and pH in order to concentrate the sample in a narrow band before moving on the separation gel.

Separation was carried out in SDS-PAGE at acrylamide concentration of 10% so that bands containing molecular weights between 22 and 300 kDa could be separated and containing 0.4% SDS. Samples were heat denatured for about 10 minutes. Electrophoretic test was carried out at 30-35 mA in an electrophoretic room (Pharmacia). At the end of the electrophoresis the proteins were transferred on nitrocellulose filter using Western blotting technique in electrophoretic room (Pharmacia) at 200 V.

Immunoblotting assay was used to analyse the filters with so transferred proteins. After a PBS 0.1% Tween 20 washing to remove transfer buffer excess and saturation with 5% dried milk in 0.1% PBS Tween20, filters were again incubated with anti-Cathepsin D antibody (BD Transduction Laboratories) for 2 hours under shaking. After incubation with primary antibody and several washings, filters were incubated with peroxidase conjugated anti IgG antibody (Bio-rad) for 2 hours under stirring. A developing system based on increased chemiluminescence by imaging plates at various exposure times was used.

6.3. Results

In order to confirm the advantageous effect of S1P on the phagolysosome maturation after phagocytosis we used as a model the internalisation of latex beads in S1P stimulated macrophages. Beads are internalised by cells through phagocytosis in about 60 minutes. Extraction of phagosomes from these cells was carried out by ultracentrifugation on density gradient. Protein component of phagosomial portions containing both just formed and lysosome fused phagosomes was assayed by Western blotting using a Cathepsin D intralysosomial protein specific antibody. This protein in fact represent a successful phagolysosome label whose amount is proportional to the phagolysosome maturation. Results obtained are shown in panel B of FIG. 6 and it can be observed that the amount of intralysosomial protein in the phagosomial fraction from S1P treated (column 3) is higher than in non treated macrophages (column 2).

EXAMPLE 7

Analysis of Viability of Mycobacteria within D-erythro-sphingosine 1-phosphate Treated Macrophages 7.1 Analysis of sphingosine 1-phosphate (S-1P) Induced Antimicrobial Activity in Macrophage Cells against Non Pathogenic Rapidly Growing Environmental Mycobacteria (*Mycobacterium smegmatis*).

Human monocytic THP-1 leukemia line cells were used in this example as a model for macrophage response. In order to obtain macrophage phenotype, $5 \times 10^5$/ml THP-1 cells were induced to differentiate by 48 hours incubation in the presence of 20 ng/ml Phorbol Myristate Acetate (PMA). Differentiated THP-1 cells (dTHP-1) were then centrifuged three times and suspended in complete medium [RPMI 1640 (Gibco BRL) supplemented with 10% fetal bovine serum (Gibco BRL), 5 mM L-glutamine (Invitrogen), 1 mM sodium pyruvate (Gibco BRL) and non essential amino acids (Euroclone)]. dTHP-1 were then infected for 3 hours with *M. smegmatis* at the multiplicity of infection of bacterium/cell 50:1. Following infection cells were washed three times with RPMI 1640 and incubated in complete medium at 37° C. for further 1, 12 and 24 hours in the presence or absence of sphingosine-1 phosphate used at the concentration of 5 µM.

In order to assess the role of macrophage PLD activity in sphingosine 1-phosphate induced mycobacterial growth control, following the infection the cells were cultured in the presence of various concentrations of ethanol (0.3%, 0.03%, 0.003%) or 10 nM calphostin C. Ethanol, inducing the formation of phosphatidyl ethanol inactive compound is a specific inhibitor of PLD metabolic activity (Liscovitch, M., Czarny, M., Fiucci, G. and Tang, X., 2000. Phospholipase D: Molecular and cell biology of a novel gene family. *Biochem. J.* 345:401). Inhibiting activity of calphostin C is exploited by targeting PLD catalytic domain (Sciorra V. A., Hammond S. M., Morris A. J. Potent direct inhibition of mammalian phospholipase D isoenzymes by calphostin c. Biochemistry 2001; 40: 2640-46). Just after the infection and at the indicated time points, cells were 1) lysed using cold PBS containing 0.1% saponin (Sigma, Mass., USA), ii) serially diluted in PBS containing 0.01% Tween-80 (Merck, Darmstadt, Germany) and iii) plated in triplicate in Middlebrook 7H10 medium (Becton Dickinson, Md., USA) supplemented with 10% OADC formulation (0.5 mg/ml oleic acid, 50 mg/ml albumin, 20 mg/ml dextrose, 0.04 mg/ml catalase and 8.5 mg/ml sodium chloride). *M. smegmatis* colonies were enumerated after incubation for 3 days at 37° C.

As shown in FIG. 7 sphingosine 1-phosphate (S-1P, used at the concentration of 5 µM) inhibits intracellular replication of *Mycobacterium smegmatis* in THP-1 macrophage cell line. Sphingosine 1-phosphate induces antimicrobial activity in such cells though macrophage D phospholipase activation as demonstrated by the increase of mycobacterial replication after ethanol treatment (dose dependent effect) or calphostin C (used at the concentration of 10 nM). *Mycobacteria* were enumerated by assay of colony forming units performed at 1 hour (panel A), 12 hours (panel B), and 24 hours (panel C) after mycobacterial infection.

7.2 Analysis of S-1 P Induced Antimicrobial Activity in Macrophage Cells Against *Mycobacterium tuberculosis*

Human monocytic THP-1 leukemia line cells were used in this example as a model for macrophage response. In order to obtain macrophage phenotype, $5 \times 10^5$/ml THP-1 cells were induced to differentiate by 48 hours incubation in the presence of 20 ng/ml Phorbol Myristate Acetate (PMA). Differentiated THP-1 cells (dTHP-1) were then centrifuged three times and suspended in complete medium [RPMI 1640 (Gibco BRL) supplemented with 10% fetal bovine serum, 5 mM L-glutamine) (Invitrogen), 1 mM sodium pyruvate (Gibco BRL) and non essential amino acids (Euroclone), 5 µg/ml gentamicin (Invitrogen)]. dTHP-1 were then infected for 3 hours with H37Rv *M. tuberculosis* at the multiplicity of infection of 1:10 (panel A) or 1:1 (panel B) bacterium/cell. After infection cells were washed three times with RPMI 1640 and incubated in complete medium for further 1, 2 and 5 days (panel A) or 1 and 7 days (panel B) in the presence or absence of sphingosine 1-phosphate used at the concentration of 5 µM. Just after the infection and at the indicated time points, cells were 1) lysed using cold PBS containing 0.1% saponin (Sigma, Mass., USA), ii) serially diluted in PBS containing 0.01% Tween-80 (Merck, Darmstadt, Germany) and iii) plated in triplicate on Middlebrook 7H10 medium (Becton Dickinson, Md., USA) supplemented with 10% OADC formulation (0.5 mg/ml oleic acid, 50 mg/ml albumin, 20 mg/ml dextrose, 0.04 mg/ml catalase and 8.5 mg/ml sodium chloride). *Mycobacterium tuberculosis* colonies were enumerated after incubation for al least 21 days at 37° C.

As shown in FIG. 8 sphingosine 1-phosphate (S1P, used at the concentration of 5 µM) inhibits intracellular replication of *Mycobacterium tuberculosis* in THP-1 macrophage cell line. Panel A refers to a representative experiment using a multiplicity of infection of 1 bacterium every 10 cells. Panel B refers to a representative experiment using a multiplicity of infection of 1 bacterium per cell.

7.3 Analysis of Macrophage Bacterial Viability

In order to evaluate the bacterial viability, monocyte derived macrophages were infected for 3 hours with MTB at 1:1 macrophage/bacterium infection ratio and then treated with S1P (5 µM). At time 0 (just after infection) and after 2 and 5 days the plates containing infected cellular cultures were centrifuged at 2000 RPM for 10 minutes and the supernatant was discarded. Then 1 ml PBS and 0.1% saponin were added to each well and the contents were incubated for 20 minute at 37° C. After incubation cellular lysates were sonicated for 20 seconds in such a way to break any possible bacterial aggregates. Lysates thus obtained were diluted in sterile saline 1:100, 1:1000, 1:10000 with addition of 0.01% Tween 80 and plated on Middlebrook 7H10 (Difco). Plates were incubated at 37° C. for about one month and colonies enumerated.

Results

Based on the observations about the possible antimicrobial role of PLD and S1P during *Mycobacterium tuberculosis* infection it was investigated whether S1P macrophage exogenous stimulation and PLD activation were associated to a reduction of mycobacterial viability. To that object, monocytes were infected for three hours with H37Rv MTB at a multiplicity of infection of 1 *bacillus* for 1 cell. Non phagocytosed bacteria were discarded by washing the cells and the analysis of colony forming units (CFU) was carried out at time 0 (just after infection) and 2 and 5 day after infection. FIG. 9 shows that 5 days after the infection CFU number is reduced after S1P treatment according to a statistically significant manner.

7.4. Analysis of Dose Dependent Effect of S1P on Macrophages from Peripheral Blood monocytes Peripheral blood mononuclear cells were isolated from human Buffy coat blood preparations by gradient centrifugation and suspended at $5 \times 10^6$/ml in complete medium [RPMI 1640 (Gibco BRL) supplemented with 10% fetal bovine serum (Gibco BRL), 5 mM L-glutamine and Gentamicine (5 µg/ml)]. Monocytes were then separated by adherence for 1 hour in polystyrene 75 cm² flasks (Corning, Cambridge, Mass.). After incubation, non-adherent cells were removed by three washes with warm RPMI 1640. In each experiment, purification level of recovered monocyte population was analysed in flow cytometry by CD14 staining or morphological parameters analysis (FSC versus SSC) and it was found to be more than 85%. Finally, adherent monocytes were collected after 15 minute incubation at 4° C. in the presence of 5 mM EDTA in PBS. Cells then were washed, incubated in complete medium for 5-7 days in 24 well plate at the concentration of $10^6$ cells/ml to get monocyte-derived macrophages. Obtained macrophages were then infected for 3 hours with the virulent strain H37Rv *M. tuberculosis* at the multiplicity of infection of 1:1 bacterium/cell. After infection cells were washed three times with RPMI 1640 and incubated in complete medium RPMI 1640 for 5 days in the absence or presence of sphingosine 1-phosphate used at concentrations of 0.5 µM, 5 µM, and 50 µM. At the indicated time points, cells were 1) lysed using cold PBS containing 0.1% saponin (Sigma, Mass., USA) ii) serially diluted in PBS containing 0.01% Tween-80 (Merck, Darmstadt, Germany) and iii) plated in triplicate on Middlebrook 7H10 medium (Becton Dickinson, Md., USA), supplemented with 10% OADC formulation (0.5 mg/ml oleic acid, 50 mg/ml albumin, 20 mg/ml dextrose, 0.04 mg/ml catalase and 8.5 mg/ml sodium chloride). *Mycobacterium. tuberculosis* colonies were enumerated after incubation for about 21 days at 37° C.

Sphingosine 1-phosphate (S-1 P), used at the concentrations of 0.5, 5 or 50 µM inhibits intracellular replication of *Mycobacterium tuberculosis* in human monocyte-derived macrophages (MDM) from peripheral blood of healthy donors. Results are obtained from experiments performed on MDM from 4 different donors and are expressed as the means of the percentages of mycobacterial killing±standard error at the fifth day after infection. Percentage of mycobacterial killing is calculated by using the following formula: [1-(CFU from infected and S-1P stimulated MDM/CFU from infected unstimulated MDM)]×100.

The invention claimed is:

1. A method of treating a subject who has been infected with a pathogen, the method comprising administering to the subject a sphingosine derivative compound in an amount sufficient to induce an immune response in the subject,
    wherein said amount increases the bactericidal activity of macrophages in said subject, and thereby treating the infection,
    wherein the pathogen is a bacterium, and
    wherein the sphingosine derivative compound is selected from the group consisting of D-erythro sphingosine isomers, L-threo sphingosine isomers, mono-phosphates, di-phosphates, and tri-phosphates.

2. The method of claim 1 wherein the compound is D-erythro sphingosine 1-phosphate (S 1P).

3. The method of claim 1 wherein the administering of the sphingosine derivative compound induces phagolysosome maturation in pathogen infected macrophages in the subject; increases the activity of macrophage phospholipase D in pathogen infected macrophages in the subject; or increases the production of oxygen and/or nitrogen reactive intermediates in pathogen-infected macrophages in the subject.

4. The method of claim 1, wherein the bacterium is *Mycobacterium tuberculosis* or *Listeria monocytogenes*.

5. The method of claim 1, wherein the subject is a human.

6. The method of claim 1, wherein the compound is within a pharmaceutical composition further comprising a surfactant, a liposome, a stabilizer, a preservative, or an antioxidant.

7. The method of claim 1, wherein the compound is within a pharmaceutical composition formulated as a solid or a liquid preparation.

8. The method of claim 7, wherein the liquid preparation is a solution, an emulsion, or a suspension.

9. The method of claim 7, wherein the liquid preparation is administered as an aerosol.

10. The method of claim 1, wherein the compound is present at a concentration of 0.1 µM to 1 mM.

11. The method of claim 10, wherein the compound is present at a concentration of 0.1 µM to 100 µM.

12. A method of treating a human subject who is infected with *Mycobacterium tuberculosis*, the method comprising administering to the subject a therapeutically effective amount of D-erythro sphingosine 1-phosphate.

13. A method of treating a subject who has been infected with a pathogen, the method comprising administering to the subject a sphingosine derivative compound in an amount sufficient to induce an immune response in the subject and thereby treat the infection, wherein the pathogen is a bacterium, wherein the sphingosine derivative compound is selected from the group consisting of D-erythro sphingosine isomers, or L-threo sphingosine isomers, mono-phospates, di-phosphates, or triphosphates and wherein the administering of the sphingosine derivative compound induces phagolysosome maturation in pathogen infected macrophages in the subject; increases the activity of macrophage phospholipase D in pathogen infected macrophages in the subject; or increases the production of oxygen and/or nitrogen reactive intermediates in pathogen-infected macrophages in the subject.

14. A method of treating a subject who has been infected with a pathogen, the method comprising administering to the subject a sphingosine derivative compound in an amount sufficient to induce an immune response in the subject,
    wherein said amount increases the microbicidal activity of macrophages in said subject, and thereby treating the infection, and
    wherein the sphingosine derivative compound is selected from the group consisting of D-erythro sphingosine isomers, L-threo sphingosine isomers, mono-phosphates, di-phosphates, and tri-phosphates.

15. The method of claim 14 wherein the compound is D-erythro sphingosine 1-phosphate (S1P).

16. The method of claim 14 wherein the administering of the sphingosine derivative compound induces phagolysosome maturation in pathogen infected macrophages in the subject; increases the activity of macrophage phospholipase D in pathogen infected macrophages in the subject; or increases the production of oxygen and/or nitrogen reactive intermediates in pathogen-infected macrophages in the subject.

* * * * *

UNITED STATES PATENT AND TRADEMARK OFFICE
CERTIFICATE OF CORRECTION

PATENT NO. : 8,377,910 B2  Page 1 of 1
APPLICATION NO. : 10/496497
DATED : February 19, 2013
INVENTOR(S) : Maurizio Fraziano et al.

It is certified that error appears in the above-identified patent and that said Letters Patent is hereby corrected as shown below:

In the Claims

Column 17 lines 27-38 should read

1. A method of treating a subject who has been infected with a pathogen, the method comprising administering to the subject a sphingosine derivative compound in an amount sufficient to induce an immune response in the subject, wherein said amount increases the bactericidal activity of macrophages in said subject, and thereby treating the infection, wherein the pathogen is a bacterium, and wherein the sphingosine derivative compound is selected from the group consisting of D-erythro sphingosine isomers, L-threo sphingosine isomers, and mono-phosphates, di-phosphates, or tri-phosphates thereof.

Column 18 lines 32-42 should read

14. A method of treating a subject who has been infected with a pathogen, the method comprising administering to the subject a sphingosine derivative compound in an amount sufficient to induce an immune response in the subject, wherein said amount increases the microbicidal activity of macrophages in said subject, and thereby treating the infection, and wherein the sphingosine derivative compound is selected from the group consisting of D-erythro sphingosine isomers, L-threo sphingosine isomers, and mono-phosphates, di-phosphates, or tri-phosphates thereof.

Signed and Sealed this
Twenty-fourth Day of March, 2015

Michelle K. Lee
*Director of the United States Patent and Trademark Office*